(12) United States Patent
Naimark et al.

(10) Patent No.: US 6,887,857 B2
(45) Date of Patent: May 3, 2005

(54) MICROPARTICLE PROTECTION OF THERAPEUTIC AGENTS

(75) Inventors: Wendy Naimark, Cambridge, MA (US); Maria Palasis, Wellsley, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 63 days.

(21) Appl. No.: 09/845,080

(22) Filed: Apr. 27, 2001

(65) Prior Publication Data

US 2002/0182190 A1 Dec. 5, 2002

(51) Int. Cl.$^7$ .............................................. A61K 48/00
(52) U.S. Cl. ..................... 514/44; 424/486; 424/468; 424/482; 424/93.2; 435/320.1; 435/455
(58) Field of Search .......................... 514/44; 424/93.2, 424/486, 468, 482; 435/320.1, 455; 525/242; 604/265, 264

(56) References Cited

U.S. PATENT DOCUMENTS

| | | | | |
|---|---|---|---|---|
| 4,795,642 A | * | 1/1989 | Cohen | 424/455 |
| 4,838,877 A | | 6/1989 | Massau | 604/272 |
| 5,607,401 A | | 3/1997 | Humphrey | 604/239 |
| 5,637,399 A | | 6/1997 | Yoshikawa et al. | 428/369 |
| 5,671,754 A | | 9/1997 | Schmukler et al. | 128/844 |
| 5,824,049 A | * | 10/1998 | Ragheb et al. | 623/1 |
| 5,873,904 A | * | 2/1999 | Ragheb et al. | 623/1 |
| 6,004,943 A | * | 12/1999 | Shi et al. | 514/44 |
| 6,099,561 A | * | 8/2000 | Alt | 623/1.44 |
| 6,248,720 B1 | * | 6/2001 | Mathiowitz | 514/44 |
| 6,368,586 B1 | * | 4/2002 | Jacob | 424/78.08 |
| 6,369,039 B1 | * | 4/2002 | Palasis et al. | 514/44 |
| 6,372,722 B1 | * | 4/2002 | Bennett | 514/44 |
| 6,398,808 B1 | * | 6/2002 | Palasis | 623/1.46 |
| 6,500,448 B1 | * | 12/2002 | Johnson | 424/423 |
| 6,638,259 B1 | * | 10/2003 | Palasis et al. | 604/264 |
| 6,663,606 B1 | * | 12/2003 | Barry et al. | 604/264 |
| 2002/0032414 A1 | * | 3/2002 | Ragheb et al. | 604/165 |
| 2002/0055721 A1 | * | 5/2002 | Palasis et al. | 604/265 |
| 2002/0098237 A1 | * | 7/2002 | Donovan et al. | 424/484 |
| 2002/0107330 A1 | * | 8/2002 | Pinchuk et al. | 525/242 |
| 2003/0073972 A1 | * | 4/2003 | Rosenman et al. | 604/502 |

FOREIGN PATENT DOCUMENTS

| | | |
|---|---|---|
| EP | 0 465 081 A1 | 1/1992 |
| WO | WO 94/06472 | 3/1994 |
| WO | WO 98/33487 | 8/1998 |
| WO | WO 99/22655 | 5/1999 |
| WO | WO 01/30403 | 5/2001 |

OTHER PUBLICATIONS

"Standard Specification for Chemical Passivation Treatments for Stainless Steel Parts," American Society For Testing and Materials, Designation A 967–96, pp. 1–6.

Marshall, Deborah J., et al., "Biocompatibility of Cardiovascular Gene Delivery Catheters with Adenovirus Vectors: An Important Determinant of the Efficiency of Cardiovascular Gene Transfer," Molecular Therapy, vol. 1, No. 5, May 2000, Part 1 of 2 Parts, p. 423–429.

Post, Mark J. et al., "Adenovirus–Mediated Gene Therapy Through Intramyocardial Injections: Percutaneous Intramyocardial Versus Surgical Epicardial Delivery," Cardiac and Vascular Regeneration, Jun. 2000, vol. 1, No. 2, pp. 106–113.

Polybead Microspheres, Polysciences, Inc. Microspheres Catalog, 1998–2000, p. 8.

* cited by examiner

Primary Examiner—Dave Trong Nguyen
(74) Attorney, Agent, or Firm—Mayer Fortkort & Williams, PC; David B. Bonham, Esq.

(57) ABSTRACT

The present invention is directed to the use of microparticles to protect the pharmaceutical effectiveness of a pharmaceutically active agent. According to one embodiment, a pharmaceutically acceptable suspension is provided that comprises microparticles and a pharmaceutically active agent. This pharmaceutically acceptable suspension is then exposed to a component or condition that is incompatible with the pharmaceutically active agent, such that the microparticles provide a pharmaceutical effectiveness that is greater than it would have been in the absence of the microparticles. Preferably, the microparticles result in a pharmaceutical effectiveness of the pharmaceutically active agent that is at least 10% greater than the pharmaceutical effectiveness of the pharmaceutically active agent would have been in the absence of the micro particles. Polymer microparticles, such as polystyrene microparticles, are one preferred class of microparticles. The microparticles preferably range from 0.01 to 100 microns in largest dimension, more preferably 0.1 to 10 microns in largest dimension. The microparticles are preferably provided in an amount of 0.1 to 1 wt % within the suspension. Agents comprising polynucleotides, including cells, plasmids and viral vectors, are a preferred class of pharmaceutically active agent. Other embodiments on the invention are directed to pharmaceutically acceptable suspensions, medical devices for parenteral injection, and methods of treatment.

18 Claims, 1 Drawing Sheet

MICROPARTICLE PROTECTION OF THERAPEUTIC AGENTS

STATEMENT OF RELATED APPLICATIONS

This application is related to U.S. Ser. No. 09/429,178 filed Oct. 28, 1999 and entitled "Biocompatible Medical Devices". This application is also related to U.S. Ser. No. 09/503,586 filed Feb. 14, 2000, also entitled "Biocompatible Medical Devices". Each of these applications is hereby incorporated by reference in its entirety.

FIELD OF THE INVENTION

This invention relates to the protection of therapeutic agents and more particularly to novel techniques and compositions for the protection of therapeutic agents using microparticles.

BACKGROUND OF THE INVENTION

As noted in related U.S. Ser. Nos. 09/429,178 and 09/503,586, devices having metallic and polymeric components are used extensively in the medical field. In many cases, such medical devices are used for delivery of a solution or suspension containing a pharmaceutically active agent, and the pharmaceutically active agent comes into contact with the metallic or polymeric component during the course of its delivery. Metallic materials used in such devices include stainless steel and nickel-titanium superelastic alloys (e.g., nitinol). Polymeric components used in such devices include polycarbonate, polyimide, acrylonitrile/butadiene/styrene resins (ABS), poly ether ether ketone (PEEK), epoxy-based adhesives (such as FDA2 or FDA23) and nylon (such as nylon 6,6). The inventors in related U.S. Ser. Nos. 09/429,178 and 09/503,586 have found, however, that despite their reputation as being substantially inert, such materials can be incompatible to varying degrees with certain pharmaceutically active agents.

The present invention provides a simple and unexpected way of overcoming the above and other incompatibilities.

SUMMARY OF THE INVENTION

According to an embodiment of the present invention, a method is provided in which microparticles are used to protect the pharmaceutical effectiveness of a pharmaceutically active agent. The method comprises: (a) providing a pharmaceutically acceptable suspension comprising the pharmaceutically active agent and microparticles; and (b) exposing the pharmaceutically acceptable suspension to a component or condition that is incompatible with the pharmaceutically active agent, such that the microparticles result in a pharmaceutical effectiveness of the pharmaceutically active agent that is greater than it would have been in the absence of the microparticles. Preferably, the microparticles result in a pharmaceutical effectiveness of the pharmaceutically active agent that is at least 10% greater than the pharmaceutical effectiveness of the pharmaceutically active agent would have been in the absence of the microparticles.

Components incompatible with the pharmaceutically active agent include metals (such as certain stainless steel and nickel-titanium alloys), polymers (such as certain poly ether ether ketones, polyimides, epoxies, nylons, acrylonitrile/butadiene/styrene polymers and polycarbonates) and glass.

Conditions incompatible with the pharmaceutically active agent include freeze-thaw transformations.

The microparticles preferably range from 0.01 to 100 microns in largest dimension, more preferably 0.1 to 10 microns in largest dimension. The microparticles are preferably provided in an amount ranging from 0.1 to 1 wt % within the suspension. Polymer microparticles, such as polystyrene microparticles, are one preferred class of microparticles.

According to another embodiment of the invention, a method of treatment is provided. The method comprises: (a) providing a pharmaceutically acceptable suspension comprising a pharmaceutically active agent and microparticles; (b) providing a medical device having a component that is incompatible with the pharmaceutically active agent; and (c) parenterally injecting the pharmaceutically active agent into a patient via the device while at the same time removing the microparticles from the pharmaceutically acceptable suspension. Preferred devices include parenteral injection devices, such as vascular catheters and syringes.

According to another embodiment of the invention, a device for parenteral injection is provided that comprises: (a) a pharmaceutically acceptable suspension comprising a pharmaceutically active agent and microparticles; (b) a device component that contacts the suspension and is incompatible with the pharmaceutically active agent; and (c) a separator that acts to remove the microparticles from the pharmaceutically acceptable suspension prior to parenteral injection.

According to another embodiment of the invention, a pharmaceutically acceptable suspension is provided. The suspension comprises: (a) a pharmaceutically active agent; and (b) microparticles that prevent a substantial reduction in pharmaceutical effectiveness of the pharmaceutically active agent upon being exposed to a material or condition that is incompatible with the pharmaceutically active agent.

One advantage associated with the present invention is that the efficacy of pharmaceutically active agents can be protected in a simple manner.

Another advantage of the present invention is that a pharmaceutically active agent can be stored in a storage container or delivered from a medical device that contains materials that would otherwise result in a substantial reduction in the pharmaceutical effectiveness of the pharmaceutically active agent.

Another advantage of the present invention is that a pharmaceutically active agent can be stored under conditions that would otherwise result in a substantial reduction in the pharmaceutical effectiveness of the pharmaceutically active agent.

Yet another advantage of the present invention is that an agent (i.e., microparticles) can be provided to protect the efficacy of the pharmaceutically active agent, but need not be introduced into a patient at the time of administration.

These and other embodiments and advantages of the present invention will become readily apparent to those of ordinary skill in the art upon review of the detailed description and claims to follow.

DETAILED DESCRIPTION

Figure 1:
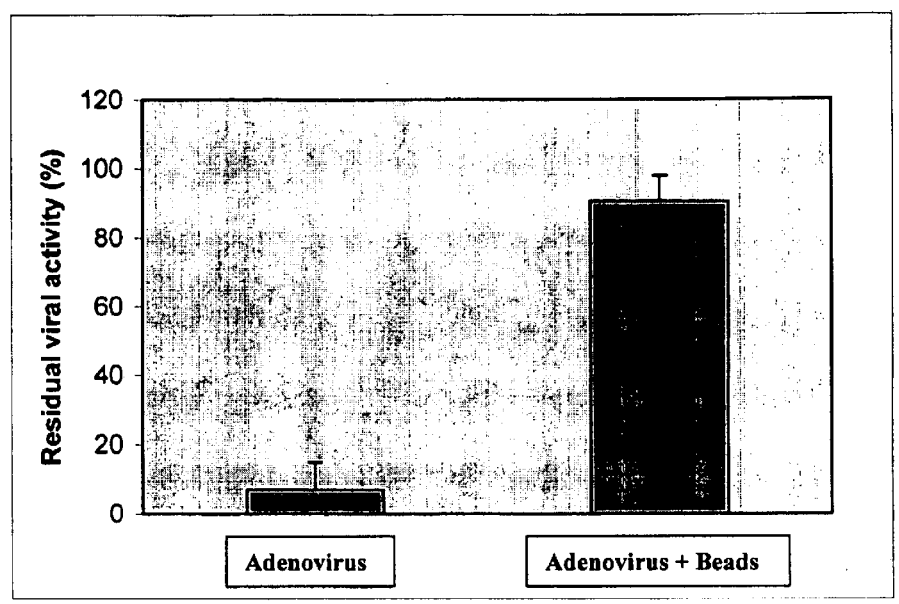
FIG. 1 is a bar graph illustrating viral activity of an adenoviral solution, with and without microparticles, according to an embodiment of the present invention.

As a preliminary matter, it is noted that "pharmaceutical article", as defined herein, means any article that comes into contact with a pharmaceutically active material.

By "pharmaceutical effectiveness" or "pharmaceutical efficacy" is meant any desired pharmaceutical result. As a specific example, the pharmaceutical effectiveness of a virus can be measured by the ability of that virus to infect cells. As another example, the pharmaceutical effectiveness of a protein can be measured by its activity within an ELISA assay.

Pharmaceutical effectiveness is said to be "substantially reduced", is "substantially lower" or is said to undergo a "substantial reduction" when it is reduced, for example, by at least 5%, more commonly 10%, 20%, 30%, 40%, 50% or more. An "incompatible component" is a component that causes a substantial reduction in pharmaceutical effectiveness upon contacting a pharmaceutically active material. A condition is an "incompatible condition" that, when encountered by a pharmaceutically active material, results in a substantial reduction in pharmaceutical effectiveness.

Pharmaceutical effectiveness is said to be "substantially increased", is "substantially higher" or is said to undergo a "substantial increase" when it is increased, for example, by at least 5%, more commonly 10%, 20%, 30%, 40%, 50% or more.

At present, many pharmaceutical articles, including various medical devices, are known in which solutions or dispersions of pharmaceutically active agents come into contact with materials prior to delivery to the body. However, as seen below in the Examples, and as further shown in related U.S. Ser. Nos. 09/429,178 and 09/503,586, where certain pharmaceutically active agents contact substrates comprising certain materials, their pharmaceutical effectiveness is substantially reduced.

For instance, it has been found that where viral particles contact certain metallic materials, such as certain stainless steel and/or nickel-titanium alloys (e.g., nitinol), or they contact certain polymeric materials, such as certain poly ether ether ketones (PEEK), polyimides, epoxies, nylons, acrylonitrile/butadiene/styrene resins (ABS) and/or polycarbonates, viral transfection may be substantially reduced. This is surprising, since it is normally assumed that such metallic and polymeric materials are substantially inert and hence unlikely to adversely affect pharmaceutically active agents.

The present invention overcomes these and other difficulties through the use of microparticles that substantially protect the pharmaceutical effectiveness of pharmaceutically active agents upon encountering materials or conditions that are incompatible with the active agents.

It is well within the skill of those of ordinary skill in the art to determine which materials, in addition to those specifically listed above, are incompatible with a given pharmaceutically active agent. Possible mechanisms for a substantial reduction in pharmaceutical effectiveness include inactivation (e.g., through denaturation, precipitation, damage, and so forth) and adsorption of the pharmaceutically active agent. It is also well within the skill of those of ordinary skill in the art to determine which conditions are incompatible with a given pharmaceutically active agent.

The present invention utilizes microparticles to substantially protect the pharmaceutical effectiveness of pharmaceutically active agents upon contacting incompatible materials or encountering incompatible conditions. The microparticles and the pharmaceutically active agent are preferably provided in a suspension. As a result of the presence of the microparticles in the suspension, the pharmaceutically active agent is substantially protected upon contact with the incompatible materials or exposure to the incompatible conditions.

By "substantially protected" is meant that effectiveness of the pharmaceutically active agent is substantially greater in the presence of the microparticles, relative to the effectiveness of the pharmaceutically active agent in the absence of the microparticles.

The microparticles of the present invention can be made of essentially any material that is effective to achieve protection of the pharmaceutically active agent, without resulting in a pharmaceutically unacceptable outcome (e.g., unacceptable levels of toxicity). These materials include materials that are not incompatible with the pharmaceutically active agent, including certain metals (e.g., gold, titanium and platinum), ceramics/glasses (e.g., quartz), polymers, and combinations of the same.

Polymers appropriate for the practice of the invention may be crosslinked or uncrosslinked, linear or branched, natural or synthetic, thermoplastic or thermosetting, or biostable, biodegradable, bioabsorbable or dissolvable.

Exemplary polymers include the following polymers and copolymers: polycarboxylic acid polymers and copolymers including polyacrylic acids (e.g., acrylic latex dispersions and various polyacrylic acid products such as HYDROPLUS, available from Boston Scientific Corporation, Natick Mass. and described in U.S. Pat. No. 5,091,205, the disclosure of which is hereby incorporated herein by reference, and HYDROPASS, also available from Boston Scientific Corporation); acetal polymers and copolymers; acrylate and methacrylate polymers and copolymers; cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydoxyalkyl celluloses; polyoxymethylene polymers and copolymers; polyimide polymers and copolymers such as polyether block imides, polybismaleinimides, polyamidimides, polyesterimides, and polyetherimides; polysulfone polymers and copolymers including polyarylsulfones and polyethersulfones; polyamide polymers and copolymers including nylon 6,6, polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (cross-linked and otherwise); anhydride polymers and copolymers including maleic anhydride polymers; polymers and copolymers of vinyl monomers including polyvinyl alcohols, polyvinyl halides such as polyvinyl chlorides, ethylene-vinylacetate copolymers (EVA), polyvinylidene chlorides, polyvinyl ethers such as polyvinyl methyl ethers, polystyrenes, styrene-butadiene copolymers, acrylonitrile-styrene copolymers, acrylonitrile-butadiene-styrene copolymers, styrene-butadiene-styrene copolymers and styrene-isobutylene-styrene copolymers, polyvinyl ketones, polyvinylcarbazoles, and polyvinyl esters such as polyvinyl acetates; polybenzimidazoles; ionomers; polyalkyl oxide polymers and copolymers including polyethylene oxides (PEO); glycosaminoglycans; polyesters including polyethylene terephthalates and aliphatic polyesters such as polymers and copolymers of lactide (which includes lactic acid as well as d-,l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of polylactic acid and polycaprolactone is one specific example); polyether polymers and copolymers including polyarylethers such as polyphenylene ethers, polyether ketones, polyether ether ketones; polyphenylene sulfides; polyisocyanates (e.g., U.S. Pat. No. 5,091,205 describes medical devices coated with one or more polyisocyanates such that the devices become instantly lubricious when exposed to body fluids); polyolefin polymers and copolymers, including polyalkylenes such as polypropylenes, polyethylenes (low and high density, low and high molecular weight), polybutylenes (such as polybut-1-ene and polyisobutylene), poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone polymers and copolymers; polyurethanes (e.g., BAYHYDROL polyurethane dispersions); p-xylylene polymers; polyiminocarbonates; copoly(ether-esters)such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid; as well as blends and copolymers of the same.

Those of ordinary skill in the art will be able to determine which polymers are most appropriate for a given pharmaceutically active material with relative ease using, for example, techniques like those used in the Examples.

Latex beads represent one preferred class of polymer microparticles that are useful in connection with the present invention. Natural latexes as well as synthetic latexes (e.g., latexes formed by emulsion polymerization from polystyrene, styrene-butadiene copolymers, acrylate polymers, polyvinyl acetate, and so forth) are preferred, with polystyrene latexes being more preferred.

The term "microparticle" as used herein refers to small particles ranging in largest dimension from 0.01 to 1000 microns, preferably 0.01 to 100 microns, more preferably 0.1 to 10 microns, and even more preferably about 1 micron. While substantially spherical particles (including both spheres and beads) are preferred, particles of any shape, including rod-shaped particles and irregularly shaped particles, are contemplated.

The microparticles and pharmaceutically active agents are provided within any physiologically acceptable liquid medium known in the art, including physiological saline, phosphate buffered saline, and solutions containing trehalose, sucrose, glycerol, tris(hydroxymethyl) aminomethane buffer and/or $MgCl_2$. Additional adjuvants known in the art are also contemplated.

Preferred amounts of the microparticles range from 0.01 to 10 wt % within the suspension, more preferably 0.1 to 1 wt %.

Preferred amounts of the pharmaceutically active agents are therapeutically effective amounts; such amounts are well within the ability of those of ordinary skill in the art to determine.

"Pharmaceutically active agents", "pharmaceutically active materials", "therapeutic agents", "drugs" and other related terms are used interchangeably herein and include genetic therapeutic agents, non-genetic therapeutic agents and cells. Pharmaceutically active agents useful in accordance with the present invention may be used singly or in combination.

Therapeutic agents include cells of human origin (autologous or allogeneic), including stem cells, or from an animal source (xenogeneic), which can be genetically engineered if desired to deliver proteins of interest. Cell types include bone marrow stromal cells, endothelial progenitor cells, myogenic cells including cardiomyogenic cells such as procardiomyocytes, cardiomyocytes, myoblasts such as skeletomyoblasts, fibroblasts, stem cells (e.g., mesenchymal, hematopoietic, neuronal and so forth), pluripotent stem cells, macrophage, satellite cells and so forth. Cells appropriate for the practice of the present invention also include biopsy samples for direct use (e.g., whole bone marrow) or fractions thereof (e.g., bone marrow stroma, bone marrow fractionation for separation of leukocytes). Where appropriate, media can be formulated as needed to maintain cell function and viability.

Therapeutic agents also include both polymeric (e.g., proteins, enzymes) and non-polymeric (e.g., small molecule therapeutics) agents and include Ca-channel blockers, serotonin pathway modulators, cyclic nucleotide pathway agents, catecholamine modulators, endothelin receptor antagonists, nitric oxide donors/releasing molecules, anesthetic agents, ACE inhibitors, ATII-receptor antagonists, platelet adhesion inhibitors, platelet aggregation inhibitors, coagulation pathway modulators, cyclooxygenase pathway inhibitors, natural and synthetic corticosteroids, lipoxygenase pathway inhibitors, leukotriene receptor antagonists, antagonists of E- and P-selectins, inhibitors of VCAM-1 and ICAM-1 interactions, prostaglandins and analogs thereof, macrophage activation preventers, HMG-CoA reductase inhibitors, fish oils and omega-3-fatty acids, free-radical scavengers/antioxidants, agents affecting various growth factors (including FGF pathway agents, PDGF receptor antagonists, IGF pathway agents, TGF-$\beta$ pathway agents, EGF pathway agents, TNF-$\alpha$ pathway agents, Thromboxane A2 [TXA2] pathway modulators, and protein tyrosine kinase inhibitors), MMP pathway inhibitors, cell motility inhibitors, anti-inflammatory agents, antiproliferative/antineoplastic agents, matrix deposition/organization pathway inhibitors, endothelialization facilitators, blood rheology modulators, as well as integrins, chemokines, cytokines and growth factors.

Therapeutic agents also include genetic therapeutic agents and proteins, such as ribozymes, anti-sense polynucelotides and polynucleotides coding for a specific product (including recombinant nucleic acids) such as genomic DNA, cDNA, or RNA. The polynucleotide can be provided in "naked" form or in connection with vector systems that enhances uptake and expression of polynucleotides. These can include DNA compacting agents (such as histones), non-infectious vectors (such as plasmids, lipids, liposomes, cationic polymers and cationic lipids) and viral vectors such as viruses and virus-like particles (i.e., synthetic particles made to act like viruses). The vector may further have attached peptide targeting sequences, antisense nucleic acids, and DNA chimeras which include gene sequences encoding for ferry proteins such as membrane translocating sequences ("MTS") and herpes simplex virus-1 ("VP22").

Further therapeutic agents include:

Anti-sense DNA and RNA tRNA or rRNA to replace defective or deficient endogenous molecules Gene delivery agents, which may be either endogenously or exogenously controlled. Examples of endogenous control include promoters that are sensitive to a physiological signal such as hypoxia or glucose elevation. Exogenous control systems involve gene expression controlled by administering a small molecule drug. Examples include tetracycline, doxycycline, ecdysone and its analogs, RU486, chemical dimerizers such as rapamycin and its analogs, etc.

Angiogenic molecules including:
  growth factors: such as acidic and basic fibroblast growth factors, vascular endothelial growth factor, epidermal growth factor, transforming growth factor alpha and beta, platelet-derived endothelial growth factor, platelet-derived growth factor, platelet derived endothelial cell growth factor, tumor necrosis factor α, hepatocyte growth factor, insulin like growth factor, placental growth factor; PR39, angiogenin, prostaglandin E1 and E2, interleukin 8, angiopoietins (I, II, III, IV, etc), androgens, proliferin, granulocyte colony stimulating factor, estrogens
  transcription factors: such as Hif1a, Del1,
  protein kinases: such as Akt Cytotoxic factors or cell cycle inhibitors, including CD inhibitors: such as p53, thymidine kinase ("TK") and other agents useful for interfering with cell proliferation The family of bone morphogenic proteins ("BMP's"): including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

Cell survival molecules: including Akt, insulin-like growth factor 1, NF-kB decoys, 1-kB, Other therapeutic agents: including Madh6, Smad6, Apo A-1, Small molecule activators or inhibitors of the genes described above including decoys.

Vectors and gene transfer agents including:
  Viral vectors: such as adenoviruses, gutted adenoviruses, adeno-associated virus, retroviruses, alpha virus (Semliki Forest, Sindbis, etc.), lentiviruses, herpes simplex virus, ex vivo modified cells (i.e., stem cells, fibroblasts, myoblasts, satellite cells, pericytes, cardiomyocytes, sketetal myocytes, macrophage, etc.), replication competent viruses (ONYX-015, etc.), and hybrid vectors.
  Nonviral vectors: artificial chromosomes and minichromosomes, plasmid DNA vectors (pCOR), cationic polymers (polyethyleneimine, polyethyleneimine (PEI) graft copolymers such as polyether-PEI and polyethylene oxide-PEI, neutral polymers PVP, SP1017 (SUPRATEK), lipids or lipoplexes, nanoparticles and microparticles with and without targeting sequences such as the protein transduction domain (PTD).

A "polynucleotide" is a nucleic acid molecule polymer, such as DNA, RNA and their analogs, having as few as 3 nucleotides, and can include both double- and single-stranded sequences. A "protein" is a polymer of as few as two (dimer) amino acid residues.

Preferably, the pharmaceutically active material is a cell or polynucleotide, more preferably a cell or polynucleotide that is present in the form of a plasmid or that is present in conjunction with virus or virus-like particles. Specific examples of preferred cells include cardiomyocytes, skeletal myoblasts, endothelial cells, and stem cells. Specific examples of preferred virus or virus-like particles include adenovirus, paroviruses such as adeno-associated virus, lentivirus, retrovirus, alpha-virus, papilloma virus, murine leukemia virus, Semliki Forest virus, and so forth.

To form the suspensions of the present invention, the microparticles and the pharmaceutically active agent are commingled in a liquid medium by essentially any known means, including stirring, shaking, and so forth.

After commingling, the suspension containing the microparticles and the pharmaceutically active agent can be stored in any manner known in the art. In one preferred embodiment, the suspension is stored in an ampoule (i.e., a sealed container, typically glass or plastic, which contains a sterile solution for parenteral injection) until the time of administration.

The use of the microparticle suspensions of the present invention with (a) manufacturing articles, including fermentors, glassware, plasticware, probes and tubing, (b) other storage and transport articles, including storage vessels, transport vessels, stoppers, lids and septums, and (c) analytical articles, including needles, pipette tips, cell culture apparatus and analytical equipment, is also contemplated.

Where the therapeutic agent is in solution or is substantially smaller than the microparticles used, separation of the therapeutic agent and microparticles can be carried out with relative ease. For example, the microparticles can be separated from the therapeutic agent by straining the microparticles from the suspension, for example, by passing the suspension through a filter of an appropriate pore size (or, as another example, through a screen of appropriate mesh) prior to administration to a patient. Preferred patients are mammalian patients, more preferably human patients.

For instance, as set forth in the Examples below, the addition of 1-micron polystyrene latex beads to a virus suspension has been shown to essentially retain virus activity when exposed to an incompatible material. In these Examples, the beads are on the order of 10 times the size of the viral particles. As a result of this large size differential, the polymeric beads can be easily excluded from an injectate by placing a size exclusion mesh at the distal end of a delivery lumen, permitting injection of the viral particles without injection of the polymeric beads. Similarly, where loss of activity is related to storage and where the medical device is not incompatible with the therapeutic agent, the beads can be separated prior to association of the therapeutic agent with the medical device.

Alternatively, by selecting biocompatible microparticles, the microparticles can be administered to a patient along with the therapeutic agent. Referring again to the Examples below, the latex polystyrene beads are tissue compatible and may be injected along with the viral particles to the patient. Injection of the beads is believed to enhance both cellular gene transfer and in vivo stability.

In many preferred embodiments of the present invention, the microparticle suspensions are administered to patients via drug-delivery medical devices and accessories. Contemplated medical devices are numerous. For example, the medical devices contemplated for use in connection with the present invention can be those used for systemic treatment or those used for local treatment of a tissue or organ. Non-limiting examples include tumors; organs including but not limited to the heart, lung, brain, liver, kidney, bladder, urethra and ureters, eye, intestines, stomach, pancreas, ovary, and prostate; skeletal muscle; smooth muscle; breast; cartilage; and bone.

Essentially any medical device for parenteral injection (i.e., a administration by a route other than the alimentary canal, including subcutaneous, intramuscular, intravenous, intravascular, intraorbital, intracapsular, intraspinal and intrasternal administration) is contemplated for use in connection with the present invention.

Preferred medical devices include catheters, including endoluminal catheters such as needle injection catheters (e.g., for endocardial, epicardial, and pericardial agent administration), balloon catheters, diagnostic catheters and perfusion catheters, conventional needle syringes, hypodermic needles, intravenous injection devices, biopsy needles and devices, tissue ablation devices, aspirating needles, stents, and so forth. Specific examples of devices for drug delivery to the heart include, for example, those found in the following patents and patent applications: U.S. Pat. No. 5,450,846, U.S. Pat. No. 5,840,059, U.S. Pat. No. 5,878,751, U.S. Pat. No. 5,551,427, U.S. Pat. No. 5,931,834, U.S. Pat. No. 5,925,012, U.S. Pat. No. 5,925,033, U.S. Pat. No. 5,538,504, WO 99/39624, WO 99/44656, WO 99/21510, WO 99/29251, EP A 99-06 0895752, and EP A 99-01 0888750, each of which is incorporated herein by reference.

In some cases, the microparticles are provided because the entire medical device is composed of an incompatible material. In other cases, only a portion of the medical device is composed of such incompatible materials.

The present invention is particularly useful in connection with viral delivery from percutaneous transcatheter devices.

In other preferred embodiments of the present invention, the microparticles are used to protect the effectiveness of pharmaceutically active agents under conditions related to storage. For example, the microparticles can be used to protect the activity of virus suspensions during storage and during freeze-thaw.

Below are Examples directed to a specific embodiment for carrying out the present invention. The Examples are offered for illustrative purposes only, and are not intended to limit the scope of the present invention in any way.

The Examples are directed to the protection of adenoviral vectors. Adenoviral vectors are a highly efficient way to transfer genetic material. Systemic delivery of adenoviral vectors is not preferable due to non-target organ infection. On the other hand, administration of adenovirus gene therapies using a medical device platform provides a means of site-specific delivery with minimal systemic leakage. However, vector instability persists as a major limitation of this strategy. Specifically, as noted in U.S. Ser. No. 09/429,178 and U.S. Ser. No. 09/503,586, medical devices have been shown to negatively impact adenoviral activity. See also Marshall et al., Molecular Therapy 2000, 1(5): 423–429.

EXAMPLE 1

A CMV-LacZ adenovirus (i.e., an adenoviral vector driven by a cytomegalovirus promoter and β-galactosidase reporter gene based on the LacZ enzyme) is used as a stock virus in this example.

An adenoviral solution having an $Ad_{CMV\text{-}LacZ}$ titer of $1\times10^9$ functional units per milliliter (fu/ml) in PBS (−/−) was prepared.

At the same time a suspension is prepared by combining the following: (a) 90 vol % adenoviral solution at a titer appropriate to give a final titer of $1\times10^9$ fu/ml and (b) 10 vol % Fluoresbrite™ YG Microspheres from Polysciences Inc., which contains 1.0-micron fluorescent polystyrene beads at a concentration of 2.5% solids in water. This combination results in a suspension that contains a final adenovirus titer of $1\times10^9$ fu/ml as well as 0.25% solids as microspheres (due to the 10:1 dilution of the bead solution).

Boston Scientific Corporation Stiletto™ direct injection catheters, which have a proximal portion formed from heat-treated stainless steel and a distal portion formed from a nitinol hypotube, were filled with the each of the above and incubated for 30 minutes at 37° C.

Catheter effluents were then collected and titered on HeLa cells (human epidermoid carcinoma cells). For this purpose, HeLa cells were first plated out in well plates at 70% confluency the day before the experiment. Prior to contacting the HeLa cells, the viral solution was diluted appropriately in infection media (Dulbecco's Modified Eagle's Medium +2% Fetal Bovine Serum) to achieve a result of 100 to 1000 infected cells per well. The diluted virus was added to the HeLa cells in the wells and incubated at 37° C. for 1 hour. 5 mls of DMEM+10% FBS were then added to each well, followed by incubation for 24–30 hours at 37° C. After aspiration of the media, the cells were fixed in 0.5% glutaraldehyde in PBS (phosphate buffered saline) for 10 minutes. The cells were washed twice in PBS and stained using an X-gal staining solution overnight at 37° C. (X-gal is 5-bromo-4-chloro-3-indolyl-β-D-galactoside, which is hydrolyzed by β-galactosidase to form a blue product). Blue cells (i.e., galactosidase-positive cells) were counted the next day to determine the titer.

Viral activity for both the adenoviral solution and the adenoviral/bead suspension was measured as a function of beta-galactosidase-positive cells and residual activity was calculated as a percentage of controls incubated in polypropylene Eppendorf tubes (used here as a standard/control) under the same conditions. The results for both the adenoviral solution and the adenoviral/bead suspension are presented in FIG. 1. As can be seen, incubation of the adenovirus solution within the Stiletto™ catheter-leads to an essentially complete loss of virus activity. In contrast, the addition of 1 micron polystyrene latex beads to the adenovirus solution results in an essentially complete retention of virus activity.

EXAMPLE 2

Efficacy of adenovirus delivery from a standard needle was performed in a mouse model. An adenoviral solution and an adenoviral suspension containing beads (10 vol % Fluoresbrite™ YG Microspheres), each having an $Ad_{CMV\text{-}LacZ}$ titer of $10^9$ fu/50 µl, were prepared. Mice were anesthetized and a left thoracotomy was used to expose the heart. Direct epicardial injections (1×50 µl) were made into the left ventricle. Animals were sacrificed 7 days following the procedure. Whole hearts were retrieved and assayed by spectroscopic absorption at 420 nm to quantify the total amount of beta-galactosidase expressed. Absorption data are given below on the basis of both sample size (150 µl) and mg protein (determined using a standard protein assay). These data indicate that beta-galactosidase expression is higher for the injections containing beads.

|  | 420 nm absorption/150 µl | β-gal (A420/mg protein) |
| --- | --- | --- |
| Adenovirus | 55.49 (51.74; 59.23) | 4.0 (3.3; 4.6) |
| Adenovirus plus beads | 93.03 (110.26; 75.79) | 8.1 (9.0; 7.1) |

Although various embodiments are specifically illustrated and described herein, it will be appreciated that modifications and variations of the present invention are covered by the above teachings and are within the purview of the appended claims without departing from the spirit and intended scope of the invention.

What is claimed is:

1. A method of using polymer microparticles to protect pharmaceutical effectiveness of a pharmaceutically active agent comprising:

combining in a physiologically acceptable liquid medium (a) a pharmaceutically active agent with (b) previously formed polymer microparticles to form a pharmaceutically acceptable suspension; and introducing said pharmaceutically acceptable suspension into an endoluminal drug delivery catheter for delivery, either with or without said polymer microparticles, of said pharmaceutically acceptable suspension to a patient, wherein introduction of said pharmaceutically acceptable suspension into said endoluminal drug delivery catheter results in contact of said pharmaceutically acceptable suspension with an incompatible component of said endoluminal drug delivery catheter that is incompatible with said pharmaceutically active agent, wherein said incompatible component comprises a metal or a polymer, and wherein said polymer microparticles protect the pharmaceutical effectiveness of said pharmaceutically active agent upon said contact of said pharmaceutically acceptable suspension with said incompatible component.

2. The method of claim 1, wherein said incompatible component comprises a metal.

3. The method of claim 2, wherein said metal is selected from stainless steel and nickel-titanium superalloy.

4. The method of claim 1, wherein said incompatible component comprises a polymer.

5. The method of claim 4, wherein said polymer is selected from polyether ether ketone, polyimide, epoxy, nylon, acrylonitrile/butadiene/styrene polymers and polycarbonate.

6. The method of claim 1, wherein said polymer microparticles are latex beads.

7. The method of claim 1, wherein said polymer microparticles are polystyrene microparticles.

8. The method of claim 1, wherein said polymer microparticles range from 0.01 to 100 microns in largest dimension.

9. The method of claim 1, wherein the polymer microparticles range from 0.1 to 0 microns in largest dimension.

10. The method of claim 1, wherein the polymer microparticles are provided in an amount of 0.1 to 1 wt % in said suspension.

11. The method of claim 1, wherein the pharmaceutically active agent comprises a polynucleotide.

12. The method of claim 11, wherein the pharmaceutically active agent is a cell, a plasmid or a viral vector.

13. The method of claim 12, wherein the pharmaceutically active agent is a viral vector selected from an adenoviral vector and an adeno-associated viral vector.

14. The method of claim 1, wherein said microparticles are polystyrene microparticles and wherein said pharmaceutically active agent is selected from a cell, a plasmid and a viral vector.

15. The method of claim 1, wherein the polymer microparticles are provided in an amount of 0.01 to 10 wt % in said suspension.

16. The method of claim 1, wherein said endoluminal drug delivery catheter is a needle injection catheter.

17. The method of claim 16, wherein said needle injection catheter is adapted for endocardial, epicardial, or pericardial administration.

18. The method of claim 1, wherein said endoluminal drug delivery catheter is adapted for parenteral injection.

* * * * *

UNITED STATES PATENT AND TRADEMARK OFFICE
CERTIFICATE OF CORRECTION

PATENT NO. : 6,887,857 B2
DATED : May 3, 2005
INVENTOR(S) : Wendy Naimark et al.

It is certified that error appears in the above-identified patent and that said Letters Patent is hereby corrected as shown below:

Column 10,
Line 33, after "catheter", delete "-".

Signed and Sealed this

Twenty-seventh Day of December, 2005

JON W. DUDAS
*Director of the United States Patent and Trademark Office*